United States Patent [19]

Schiehser

[11] Patent Number: 5,100,883
[45] Date of Patent: Mar. 31, 1992

[54] FLUORINATED ESTERS OF RAPAMYCIN

[75] Inventor: Guy A. Schiehser, Yardley, Pa.

[73] Assignee: American Home Products Corporation, New York, N.Y.

[21] Appl. No.: 682,793

[22] Filed: Apr. 8, 1991

[51] Int. Cl.[5] .................. A61K 35/74; C07D 491/14
[52] U.S. Cl. .................................. 514/183; 514/321; 540/456
[58] Field of Search .................. 540/456; 514/183, 321

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,316,885 | 2/1982 | Rakhit | 424/122 |
| 4,401,653 | 8/1983 | Eng | 424/114 |
| 4,650,803 | 3/1987 | Stella et al. | 546/90 |
| 4,885,171 | 12/1989 | Surendra et al. | 424/122 |

OTHER PUBLICATIONS

J. Antibiot. 28, 721-726, 727-732 (1975).
J. Antibiot. 31, 539-545 (1978).
Can. J. Physiol. Pharmacol. 55, 48 (1977).
FASEB 3, 3411, 5256 (1989).
Lancet pp. 1183-1185 (1978).
Med. Sci. Res. 17:877 (1989).

*Primary Examiner*—Robert T. Bond
*Attorney, Agent, or Firm*—Arnold S. Milowsky

[57] ABSTRACT

A compound of the structure

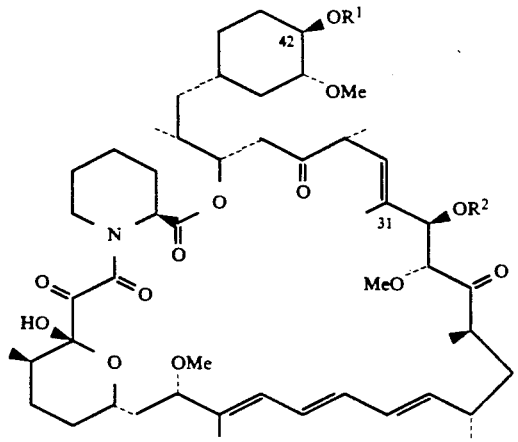

wherein
$R^1$ and $R^2$ are each, independently, hydrogen or

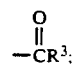

$R^3$ is a mono-, di-, poly-, or per-fluorinated alkyl group with the proviso that $R^1$ and $R^2$ are both not hydrogen, which by virtue of its immunosuppressive activity is useful in treating transplantation rejection, host vs. graft disease, autoimmune diseases and diseases of inflammation; by virtue of its antitumor activity is useful in treating solid tumors; and by virtue of its antifungal activity is useful in treating fungal infections.

11 Claims, No Drawings

FLUORINATED ESTERS OF RAPAMYCIN

BACKGROUND OF THE INVENTION

This invention relates to novel esters of rapamycin and a method for using them in the treatment of transplantation rejection, host vs. graft disease, autoimmune diseases, diseases of inflammation, solid tumors, and fungal infections.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions.

DESCRIPTION OF THE INVENTION

This invention provides derivatives of rapamycin which are useful as immunosuppressive, anti-inflammatory, and antifungal agents having the structure

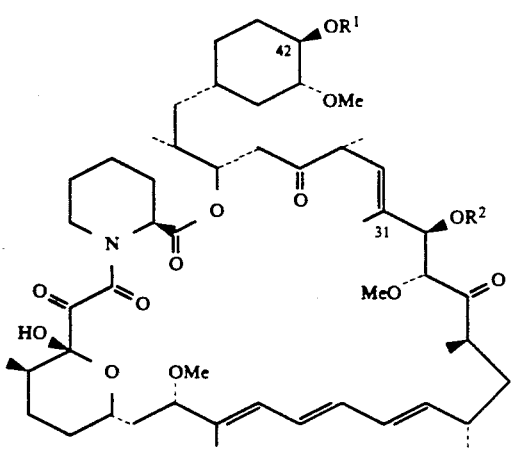

wherein $R^1$ and $R^2$ are each, independently, hydrogen or

$R^3$ is a mono-, di-, poly-, or per-fluorinated alkyl group of 1-10 carbon atoms; with the proviso that $R^1$ and $R^2$ are both not hydrogen.

Of these compounds, preferred members are those in which $R^2$ is hydrogen; those in which $R^3$ is a mono-, di-, poly-, or per-fluorinated alkyl group of 1-6 carbon atoms; and those in which $R^2$ is hydrogen and $R^3$ is a mono-, di-, poly-, or per-fluorinated alkyl group of 1-6 carbon atoms.

The compounds of this invention acylated at the 42-position can be prepared by acylating rapamycin with an acylating agent having the general structure

where X is OH, in the presence of a coupling reagent, such as CMC (1-cyclohexyl-3-(2-morpholinoethyl)carbodiimide metho-para-toluenesulphonate). The compounds of this invention also can be prepared by using an anhydride of the above described carboxylic acid as the acylating species. In addition, the acylating species can be an acid halide, where X can be Cl, Br, or I. Alternatively, reagents such as Ishikawa's Reagent (N,N-diethyl-1,1-2,3,3,3-hexafluoropropylamine) can be used as an acylating reagent to give compounds of this invention.

The compounds of this invention acylated at both the 31- and 42-positions can be prepared by the methods described above by increasing variables such as reaction time, temperature, and quantity of acylating agent.

The 31-acylated compounds of this invention can be prepared by protecting the 42-alcohol of rapamycin with a protecting group, such as with a tert-butyl dimethylsilyl group in the presence of a base, such as imidazole, followed by acylation of the 31-position with an acylating agent having the general structure shown above. Removal of the protecting group provides the 31-acylated compounds. In the case of the tert-butyl dimethylsilyl protecting group, deprotection can be accomplished under mildly acidic conditions, such as with a mixture of aqueous acetic acid and THF.

Having the 31-position acylated and the 42-position deprotected, the 42-position can be reacted with a different acylating agent than was reacted with the 31-alcohol, to give compounds having different acyl moieties at the 31- and 42-positions. Alternatively, the 42-acyl compounds, prepared as described above, can be reacted with an acylating agent having a different structure to provide compounds having different acyl moieties at the 31- and 42-positions.

The acylating groups used to prepare the compounds of the invention are commercially available or can be prepared by methods that are disclosed in the literature.

Immunosuppressive activity was evaluated in an in vitro standard pharmacological test procedure to measure lymphocyte proliferation (LAF) and in two in vivo standard pharmacological test procedures. The first in vivo procedure was a popliteal lymph node (PLN) test procedure which measured the effect of compounds of this invention on a mixed lymphocyte reaction and the second in vivo procedure evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. The results are expressed by the following ratio, or as the percent inhibition of lymphoproliferation at 1 µM.

$$\frac{^3H\text{-control thymus cells} - ^3H\text{-rapamycin-treated thymus cells}}{^3H\text{-control thymus cells} - ^3H\text{-test compound-treated cells}}$$

A mixed lymphocyte reaction (MLR) occurs when lymphoid cells from genetically distinct animals are combined in tissue culture. Each stimulates the other to undergo blast transformation which results in increased DNA synthesis that can be quantified by the incorporation of tritiated thymidine. Since stimulating a MLR is a function of disparity at Major Histocompatibility antigens, an in vivo popliteal lymph node (PLN) test procedure closely correlates to host vs. graft disease. Briefly, irradiated spleen cells from BALB/c donors are injected into the right hind foot pad of recipient C3H mice. The drug is given daily, p.o. from Day 0 to Day 4. On Day 3 and Day 4, tritiated thymidine is given i.p., b.i.d. On Day 5, the hind popliteal lymph nodes are removed and dissolved, and radioactivity counted. The corresponding left PLN serves as the control for the PLN from the injected hind foot. Percent suppression is calculated using the non-drug treated animals as allogenic control. Rapamycin at a dose of 6 mg/kg, p.o. gave 86% suppression, whereas cyclosporin A at the same dose gave 43% suppression. Results are expressed by the following ratio:

$$\frac{^3H\text{-PLN cells control C3H mouse} - ^3H\text{-PLN cells rapamycin-treated C3H mouse}}{^3H\text{-PLN cells control C3H mouse} - ^3H\text{-PLN cells test compound-treated C3H mouse}}$$

The second in vivo test procedure is designed to determine the survival time of pinch skin graft from male DBA/2 donors transplanted to male BALB/c recipients. The method is adapted from Billingham R. E. and Medawar P. B., J. Exp. Biol. 28:385–402, (1951). Briefly, a pinch skin graft from the donor is grafted on the dorsum of the recipient as a homograft, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rejection day. The mean graft survival time (number of days±S.D.) of the drug treatment group is compared with the control group.

The following table summarizes the results of representative compounds of this invention in these three standard test procedures.

TABLE 1

| Compound | LAF* (ratio) | PLN* (ratio) | Skin Graft (days + SD) |
|---|---|---|---|
| Example 1 | 40 | 1.28 | 10.33 ± 1.0 |
| Example 2 | 2.3 | 1.03 | 12.0 ± 1.3 |
| Example 3 | 27 | 0.23 | + |
| Example 4 | 14.8 | 0.96 | + |
| Rapamycin | 1 | 1 | 12.0 ± 1.7 |

*Calculation of ratios was described supra.
+ Not evaluated

The results of these standard pharmacological test procedures demonstrate immunosuppressive activity both in vitro and in vivo for the compounds of this invention. Positive ratios in the LAF and PLN test procedures indicate suppression of T cell proliferation. As a transplanted pinch skin grafts are typically rejected within 6–7 days without the use of an immunosuppressive agent, the increased survival time of the skin graft when treated with the compounds of this invention further demonstrates their utility as immunosuppressive agents.

Because the compounds of this invention are structurally similar to rapamycin and have a similar activity profile to rapamycin, the compounds of this invention also are considered to have antitumor and antifungal activities.

Based on the results of these standard pharmacological test procedures, the compounds are useful in the treatment of transplantation rejection such as, heart, kidney, liver, bone marrow, and skin transplants; autoimmune diseases such as, lupus, rheumatoid arthritis, diabetes mellitus, myasthenia gravis, and multiple sclerosis; and diseases of inflammation such as, psoriasis, dermatitis, eczema, seborrhea, inflammatory bowel disease; solid tumors; and fungal infections.

The compounds may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

In addition, the compounds of this invention may be employed as a solution, cream, or lotion by formulation with pharmaceutically acceptable vehicles containing 0.1-5 percent, preferably 2%, of active compound which may be administered to a fungally affected area.

The following examples illustrate the preparation of representative compounds of this invention.

EXAMPLE 1

Rapamycin, 42-ester with trifluoroacetic acid

Method A

To a solution of 274 mg (0.3 mmol) of rapamycin in 10 ml of methylene chloride is added 63 mg (0.3 mmol, 43 μl) of trifluoroacetic anhydride and then 39 mg (0.3 mmol) of diisopropylethylamine (Hunig's base). The mixture is stirred for 30 min and then an additional 78 mg (0.6 mmol, 106 μl) of Hunig's base is added followed by 63 mg (43 μl, 0.3 mmol) of trifluoroacetic anhydride. After 30 min the reaction mixture is diluted with ethyl ether and aqueous sodium bicarbonate. The mixture is extracted with ethyl ether (3 times) and the combined organic extracts are washed with aqueous sodium bicarbonate. The resulting extract is dried over magnesium sulfate and removed of solvent in vacuo to give a solid foam.

Flash chromatography on silica gel using ethyl ether:hexane (4:1) as the eluant gave 96 mg of product which is recrystallized from cyclohexane:hexane (1:1) to give 68 mg of the title compound: m.p. 87°-91° C.

Anal Calcd. for $C_{53}H_{78}F_3NO_{14}$: C, 63.02; H, 7.78; N, 1.39. Found: C, 62.85; H, 7.84; N, 1.41.

Method B

A solution of 914 mg (1 mmol) of rapamycin, 423 mg (1 mmol) of CMC (1-cyclohexyl-3-(2-morpholinoethyl)carbodiimide metho-para-toluenesulphonate), 20 mg of dimethylaminopyridine and 101 mg (140 μl, 1 mmol) of triethylamine in 50 ml of methylene chloride is treated dropwise with 114 mg (1 mmol, 77 μl) of trifluoroacetic acid. The mixture is maintained with stirring for 17 h. An additional 1 mmol of CMC, 20 mg of dimethylaminopyridine, 1 mmol of triethylamine and 1 mmol of trifluoroacetic acid is added. Additional trifluoroacetic acid (1 mmol) is added at 0.5 h intervals until conversion is complete.

The mixture is diluted with water and ethyl ether and is extracted with ethyl ether. The ethereal extract is washed with water, 0.5N hydrochloric acid and finally with saturated aqueous sodium bicarbonate. The solution is dried over magnesium sulfate, filtered and evaporated to give 870 mg of a white foam. The crude product is subjected to flash chromatography using hexane:ethyl ether (1:4) as the eluant. The obtained product is recrystallized from hexane:cyclohexane (1:1) to afford 397 mg of the title compound: m.p. 88°-91° C.

Anal. Calcd. for $C_{53}H_{78}F_3NO_{14}$: C, 63.02; H, 7.78; N, 1.39. Found: C, 63.21; H, 7.67; N, 1.34.

The following representative compounds can be prepared from rapamycin and the appropriate carboxylic acid by employing Method B used to prepare the title compound in Example 1.

Rapamycin, 42-ester with perfluorovaleric acid
Rapamycin, 42-ester with perfluorodecanoic acid
Rapamycin, 42-ester with perfluorooctanoic acid
Rapamycin, 42-ester with 9-H perfluorononanoic acid

EXAMPLE 2

Rapamycin, 42-ester with 2,3,3,3-tetrafluoropropanoic acid

To a solution of 914 mg (1 mmol) of rapamycin in 20 ml of methylene chloride is added 245 mg (1.1 mmol) of Ishikawa Reagent (N,N-diethyl 1,1,2,3,3,3-hexafluoropropylamine). After 1 hr, an additional 84 mg (0.4 mmol) of Ishikawa Reagent is added. The mixture is stirred for 2 h and then is diluted with ethyl ether and aqueous sodium bicarbonate. The ethyl ether layer is separated and the aqueous layer is reextracted with ethyl ether (2 times). The combined ethereal extracts are dried over magnesium sulfate, filtered and removed of solvent in vacuo to give 762 mg of a solid foam.

A portion of the crude product is subjected to silica gel chromatography using hexane:ethyl ether (1:4) as the eluant to give 310 mg of product (Rf=0.28 hexane:ethyl ether(1:4)). Recrystallization from hexane:cyclohexane (3:1) gives, after high vacuum drying over phosphorus pentoxide, 246 mg of the title compound: m.p. 87°-90° C.;

Anal. Calcd. for $C_{54}H_{79}F_4NO_{14}$: C, 62.23; H, 7.64, N, 1.34. Found: C, 62.97; H, 7.69; N, 1.07.

EXAMPLE 3

Rapamycin, 42-ester with difluoroacetic acid

A solution of 914 mg (1 mmol) of rapamycin, 846 mg (2 mmol) of CMC, 40 mg of dimethylaminopyridine and 202 mg (280 μl, 2 mmol) of triethylamine in 50 ml of methylene chloride is treated dropwise with 192 mg (126 μl, 2 mmol) of difluoroacetic acid. The mixture is maintained with stirring for 1 h and additional triethylamine and difluoroacetic acid is added until the conversion is complete.

The mixture is diluted with water and ethyl ether and is extracted with ethyl ether. The ethereal extract is washed with water, 0.5N hydrochloric acid and finally with saturated aqueous sodium bicarbonate. The solution is dried over magnesium sulfate, filtered and evaporated to give a white foam. The crude product is crystallized from cyclohexane to give 703 mg product. Flash chromatography using hexane:ethyl ether(1:4) as the eluant followed by recrystallization from cyclohexane affords the title compound: m.p. 87°–89° C.

Anal. Calcd. for $C_{53}H_{79}F_2NO_{14}$: C, 64.16; H, 8.03; N, 1.41. Found: C, 64.46; H, 8.05; N, 1.42.

EXAMPLE 4

Rapamycin, 42-ester with pentafluoropropionic acid

A solution of 914 mg (1 mmol) of rapamycin, 846 mg (2 mmol) of CMC, 40 mg of dimethylaminopyridine and 202 mg (280 μl, 2 mmol) of triethylamine in 50 ml of methylene chloride is treated dropwise with 328 mg (210 μl, 2 mmol) of pentafluoropropionic acid. The mixture is maintained with stirring for 1 h and additional triethylamine and difluoroacetic acid is added until the conversion is complete.

The mixture is diluted with water and ethyl ether and is extracted with ethyl ether. The ethereal extract is washed with water, 0.5N hydrochloric acid and finally with saturated aqueous sodium bicarbonate. The solution is dried over magnesium sulfate, filtered and evaporated to give a white foam. The crude product is crystallized from cyclohexane to give 703 mg product. Flash chromatography using hexane:ethyl ether (1:4) as the eluant followed by recrystallization from hexane:cyclohexane (1:1) affords the title compound: m.p. 90°–97° C.

Anal. Calcd. for $C_{54}H_{78}F_5NO_{14}$: C, 61.18; H, 7.42; N, 1.32. Found: C, 61.45; H, 7.42; N, 1.33.

What is claimed is:

1. A compound of the formula

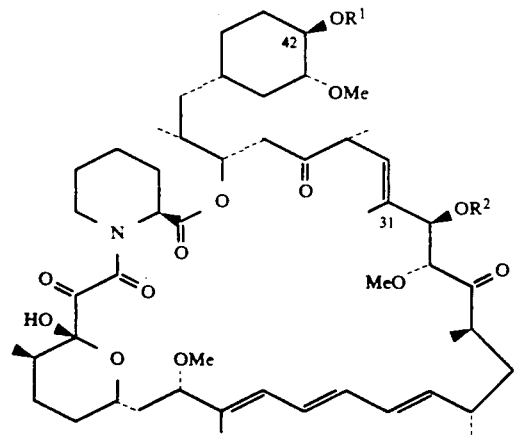

wherein
$R^1$ and $R^2$ are each, independently, hydrogen or

$R^3$ is a mono-, di-, poly-, or per-fluorinated alkyl group of 1–10 carbon atoms; with the proviso that $R^1$ and $R^2$ are both not hydrogen.

2. A compound of claim 1 where $R^2$ is hydrogen.

3. A compound of claim 1 where $R^3$ is a mono-, di-, poly-, or per-fluorinated alkyl group of 1–6 carbon atoms.

4. A compound of claim 1 where $R^2$ is hydrogen and $R^3$ is a mono-, di-, poly-, or per-fluorinated alkyl group of 1–6 carbon atoms.

5. A compound of claim 1 which is rapamycin, 42-ester with trifluoroacetic acid.

6. A compound of claim 1 which is rapamycin, 42-ester with 2,3,3,3-tetrafluoropropanoic acid.

7. A compound of claim 1 which is rapamycin, 42-ester with difluoroacetic acid.

8. A compound of claim 1 which is rapamycin, 42-ester with pentafluoropropionic acid.

9. A method of treating transplantation rejection, host vs. draft disease, autoimmune diseases, and diseases of inflammation in a mammal by administering an effective amount of a compound having the formula

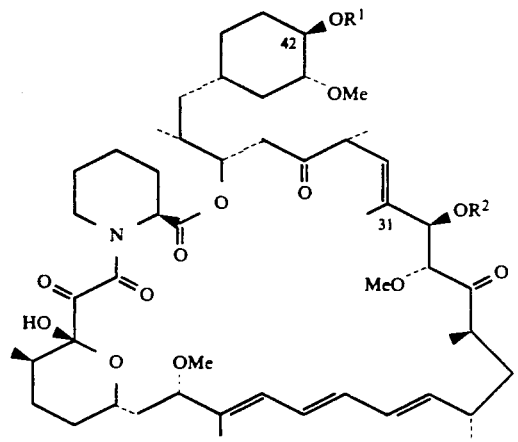

wherein
$R^1$ and $R^2$ are each, independently, hydrogen or

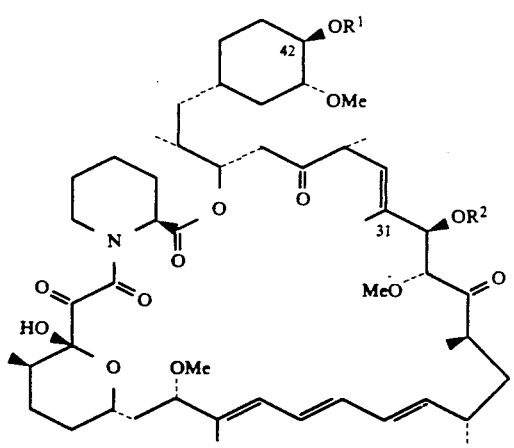

$R^3$ is a mono-, di-, poly-, or per-fluorinated alkyl group of 1–10 carbon atoms; with the proviso that $R^1$ and $R^2$ are both not hydrogen.

10. A pharmaceutical composition for use as an immunosuppressive agent comprising an immunosuppressive amount of a compound of claim 1.

11. A composition as claimed in claim 10 in unit dosage form.

* * * * *